(12) United States Patent
Kim

(10) Patent No.: US 10,905,363 B2
(45) Date of Patent: Feb. 2, 2021

(54) POC DIAGNOSTIC DEVICE ADAPTABLE TO ENVIRONMENTAL CHANGES AND CONTROL METHOD THEREOF

(71) Applicant: OSANG HEALTHCARE CO., LTD., Anyang-si (KR)

(72) Inventor: Keun Young Kim, Seoul (KR)

(73) Assignee: Osang Healthcare Co., Ltd. (KR)

( * ) Notice: Subject to any disclaimer, the term of this patent is extended or adjusted under 35 U.S.C. 154(b) by 565 days.

(21) Appl. No.: 15/792,485

(22) Filed: Oct. 24, 2017

(65) Prior Publication Data

US 2018/0110448 A1 Apr. 26, 2018

(30) Foreign Application Priority Data

Oct. 24, 2016 (KR) ........................ 10-2016-0138680

(51) Int. Cl.
*A61B 5/1491* (2006.01)
*A61B 5/145* (2006.01)
*G01K 3/10* (2006.01)

(52) U.S. Cl.
CPC ........ *A61B 5/1491* (2013.01); *A61B 5/14532* (2013.01); *G01K 3/10* (2013.01); *A61B 2560/0252* (2013.01)

(58) Field of Classification Search
CPC ... A61B 5/1491; A61B 5/1468; A61B 5/1486; A61B 5/14865; A61B 5/1495; A61B 5/14532; A61B 2560/0252; G01K 3/10
USPC .................................................. 600/365, 347
See application file for complete search history.

(56) References Cited

U.S. PATENT DOCUMENTS

| 7,727,147 B1* | 6/2010 | Osorio | A61B 5/14528 600/345 |
| 7,883,015 B2* | 2/2011 | Ackermann | G16H 40/40 235/439 |
| 8,348,842 B1* | 1/2013 | Osorio | A61B 5/14528 600/345 |
| 8,470,241 B2* | 6/2013 | Rivas | A61B 5/14532 422/50 |

(Continued)

FOREIGN PATENT DOCUMENTS

KR 10-0980316 B1 9/2010

OTHER PUBLICATIONS

Keun Young Kim, et al., Thesis: "Study of Chronic Diseases Management System Using LPWAN," Infopia Co., Ltd., Jun. 22, 2016, 5 pages.

(Continued)

*Primary Examiner* — Navin Natnithithadha
(74) *Attorney, Agent, or Firm* — Lewis Roca Rothgerber Christie LLP

(57) ABSTRACT

The present invention relates to a point-of-care (POC) diagnostic device adaptable to environmental changes and a control method thereof. The POC diagnostic device includes a measurement unit configured to perform a POC diagnosis, an information acquisition unit configured to acquire environmental information of the POC diagnostic device, and a control unit configured to predict a temperature of the measurement unit on the basis of the environmental information acquired by means of the information acquisition unit and correct a measurement value of the measurement unit or control the POC diagnostic device on the basis of the predicted temperature of the measurement unit.

14 Claims, 5 Drawing Sheets

(56) References Cited

U.S. PATENT DOCUMENTS

| | | | | |
|---|---|---|---|---|
| 8,597,190 | B2* | 12/2013 | Rule | A61B 5/0002 600/366 |
| 8,649,997 | B2* | 2/2014 | Farrell | G01N 33/48785 702/130 |
| 8,707,392 | B2* | 4/2014 | Birtwhistle | H04W 12/003 726/3 |
| 8,801,275 | B2* | 8/2014 | Wu | G01K 7/42 374/109 |
| 8,849,459 | B2* | 9/2014 | Ramey | A61B 5/002 700/266 |
| 9,289,169 | B2* | 3/2016 | Rule | A61B 5/0002 |
| 9,632,013 | B2* | 4/2017 | Rivas | G01N 1/10 |
| 9,664,644 | B2* | 5/2017 | Sun | A61B 5/01 |
| 9,851,261 | B2* | 12/2017 | Wu | G01K 1/20 |
| 10,168,227 | B2* | 1/2019 | Wu | G01K 1/20 |
| 10,481,013 | B2* | 11/2019 | Wu | G01K 1/20 |
| 2004/0249673 | A1* | 12/2004 | Smith | G16H 40/63 705/2 |
| 2008/0217407 | A1* | 9/2008 | Ackermann | G16H 40/40 235/439 |
| 2009/0036764 | A1* | 2/2009 | Rivas | A61B 5/1455 600/365 |
| 2009/0157430 | A1* | 6/2009 | Rule | A61B 5/14546 705/3 |
| 2010/0000862 | A1* | 1/2010 | Rao | A61B 5/14532 204/403.02 |
| 2010/0268475 | A1* | 10/2010 | Kusumoto | G01N 27/3272 702/19 |
| 2010/0319436 | A1* | 12/2010 | Sun | G01N 27/308 73/61.46 |
| 2010/0324398 | A1* | 12/2010 | Tzyy-Ping | A61B 5/14532 600/365 |
| 2011/0191059 | A1* | 8/2011 | Farrell | G01N 33/48785 702/130 |
| 2012/0059237 | A1* | 3/2012 | Amir | A61B 5/0285 600/365 |
| 2012/0076171 | A1* | 3/2012 | Wu | G01K 1/20 374/183 |
| 2012/0095312 | A1* | 4/2012 | Ramey | G01K 7/42 600/365 |
| 2012/0203089 | A1* | 8/2012 | Rule | A61B 5/14532 600/366 |
| 2012/0232367 | A1* | 9/2012 | Allegri | A61B 5/145 600/365 |
| 2013/0160532 | A1* | 6/2013 | Rivas | A61B 5/14532 73/64.56 |
| 2014/0083848 | A1* | 3/2014 | Sun | G01K 3/08 204/400 |
| 2014/0275868 | A1* | 9/2014 | Rule | A61B 5/412 600/310 |
| 2014/0314119 | A1* | 10/2014 | Wu | G01N 33/48785 374/109 |
| 2015/0293055 | A1* | 10/2015 | Sun | G01N 27/308 204/408 |
| 2016/0361515 | A1* | 12/2016 | Jung | A61B 5/02055 |
| 2016/0371451 | A1* | 12/2016 | Rule | G01N 21/3577 |
| 2018/0087972 | A1* | 3/2018 | Wu | G01K 7/42 |

OTHER PUBLICATIONS

Keun Young Kim et al., Thesis: "Research on Improving Medication Adherence With the Wearable Device," Infopia Co., Ltd. Jun. 29, 2016, 4 pages.

Report entitled, "The Development of the Personal Health Record Based Smart Medication Management System," Aug. 15, 2016, 107 pages.

* cited by examiner

POC DIAGNOSTIC DEVICE ADAPTABLE TO ENVIRONMENTAL CHANGES AND CONTROL METHOD THEREOF

CROSS-REFERENCE TO RELATED APPLICATION

This application claims priority to and the benefit of Korean Patent Application No. 10-2016-0138680, filed on Oct. 24, 2016, the disclosure of which is incorporated herein by reference in its entirety.

BACKGROUND

1. Field

The present invention relates to a point-of-care (POC) diagnostic device adaptable to environmental changes and a control method thereof, and more particularly, to a POC diagnostic device adaptable to environmental changes, the POC device being capable of enhancing a measurement accuracy by adapting to environmental changes, and a control method thereof.

2. Discussion of Related Art

In recent years, as interest in point-of-care (POC) devices is increasing, the development of associated devices is also increasing.

There are typical medical diagnostic devices for diagnosing infections or diseases using blood or bodily fluid. When a drop of blood is dropped onto a strip-type diagnostic sheet inserted into such a medical diagnostic device, it is possible to check for diseases such as diabetes, hyperlipidemia, and myocardial infarction and also possible to check health status depending on the type of diagnostic sheet.

For example, diabetes can be checked for by using a blood sugar level indicating the concentration of glucose per 100 ml of blood. Normally, the blood sugar level is measured by using the amount of glucose in blood. However, glucose cannot be directly measured, and thus blood sugar is measured through an indirect method of measuring the amount of by-products obtained by glucose reacting with an enzyme. Such a measurement method is generally either an electrochemical method of measuring an electric current caused by electrons generated during a reaction between glucose and an enzyme or a photometric method of generating a colored reaction intermediate during an enzyme reaction process and measuring the color.

However, a POC diagnosis is performed at a point of care, that is, at a place where a person (i.e., a patient) undergoes diagnostic examination. Accordingly, there may be various environmental changes during the POC diagnosis that may affect the speed and variables of a chemical reaction.

Accordingly, environmental changes during the POC diagnosis may cause errors in measurement values meant for the POC diagnosis.

Much research has been conducted in order to reduce such errors, and various solutions have been proposed for measuring a temperature at a location where a chemical reaction occurs and compensating for the measured temperature. However, it is not easy to detect the actual temperature of the location where the chemical reaction occurs, and thus it is difficult to actually apply such solutions.

As a related art, there is Korean patent No. 10-0980316 (registered on Aug. 31, 2010) entitled "Strip having thermal compensating function and method for measuring blood sugar using it."

SUMMARY

The present invention is directed to providing a point-of-care (POC) diagnostic device that is adaptable to environmental changes to enhance measurement accuracy of the POC diagnostic device, and a control method thereof.

According to an aspect of the present invention, there is provided a point-of-care (POC) diagnostic device adaptable to environmental changes and including a measurement unit configured to perform a POC diagnosis; an information acquisition unit configured to acquire environmental information of the POC diagnostic device; and a control unit configured to predict a temperature of the measurement unit on the basis of the environmental information acquired by means of the information acquisition unit and correct a measurement value of the measurement unit or control the POC diagnostic device on the basis of the predicted temperature of the measurement unit.

The temperature of the measurement unit predicted by the control unit may include a current temperature and a future temperature change of the measurement unit.

The POC diagnostic device may include a plurality of modules capable of being individually activated or deactivated, and the control unit may control the activation or deactivation of the plurality of modules on the basis of the predicated temperature of the measurement unit.

The control unit may deactivate at least one of the plurality of modules when the temperature of the measurement unit is predicted to rise above a first reference value within a first reference timeframe.

The control unit may determine a module to be deactivated according to preset priorities.

The measurement unit may include a temperature adjustment unit configured to adjust the temperature of the measurement unit, and the control unit may control the temperature adjustment unit on the basis of the predicted temperature of the measurement unit.

The temperature adjustment unit may include a heater, and the control unit may drive the heater when the temperature of the measurement unit is predicted to fall below a second reference value within a second reference timeframe.

The information acquisition unit may include at least one temperature sensor configured to detect a temperature of the POC diagnostic device.

The control unit may predict the temperature of the measurement unit on the basis of whether the plurality of modules are each active or inactive and a detection value of the temperature sensor.

The information acquisition unit may further include a location sensor configured to acquire location information of the POC diagnostic device, an atmospheric pressure sensor configured to acquire atmospheric pressure information, and a humidity sensor configured to acquire humidity information.

The plurality of modules may include a display module configured to display information, a communication module configured to communicate with an external device, and a barcode module configured to recognize a barcode.

The measurement unit may include a blood sugar measurement unit configured to measure blood sugar of a person undergoing diagnostic examination.

According to another aspect of the present invention, there is provided a control method of a point-of-care (POC) diagnostic device adaptable to environmental changes, the control method including acquiring environmental information of the POC diagnostic device; predicting a temperature of a measurement unit configured to perform a POC diagnosis on the basis of the environmental information; controlling the POC diagnostic device when the temperature of the measurement unit is predicted to rise above a first reference value within a first reference timeframe or to fall below a second reference value within a second reference timeframe; performing a measurement for the POC diagnosis by means of the measurement unit; and correcting a measurement value measured by the measurement unit on the basis of the predicted temperature of the measurement unit.

The acquisition of environmental information may include detecting a temperature of the POC diagnostic device.

The controlling of the POC diagnostic device may include deactivating at least one of a plurality of modules when the temperature of the measurement unit is predicted to rise above the first reference value within the first reference timeframe.

The deactivation of at least one of a plurality of modules may include checking whether there are deactivatable modules; and deactivating at least one of the modules according to preset priorities when the modules are deactivatable.

The controlling of the POC diagnostic device may include driving a heater when the temperature of the measurement unit is predicted to fall below the second reference value within the second reference timeframe.

The performing of a measurement for the POC diagnosis by means of the measurement unit may include measuring the blood sugar of a person subject undergoing diagnostic examination.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
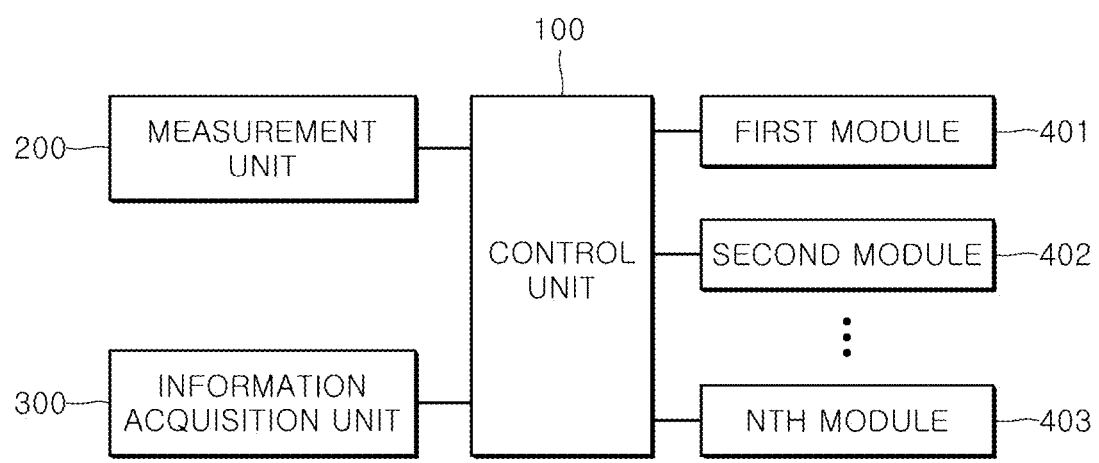
FIG. 1 is a block diagram showing a configuration of a POC diagnostic device adaptable to environmental changes according to an embodiment of the present invention.

Hereinafter, embodiments of a point-of-care (POC) diagnostic device adaptable to environmental changes and a control method thereof according to the present invention will be described with reference to the accompanying drawings. In the drawings, thicknesses of lines or sizes of elements may be exaggerated for clarity and convenience. Also, the following terms are defined considering their functions in the present invention, and may be differently defined depending on a user, the intent of an operator, or a custom. Therefore, the definition of the terms should be based on overall contents of the specification.

Figure 2:
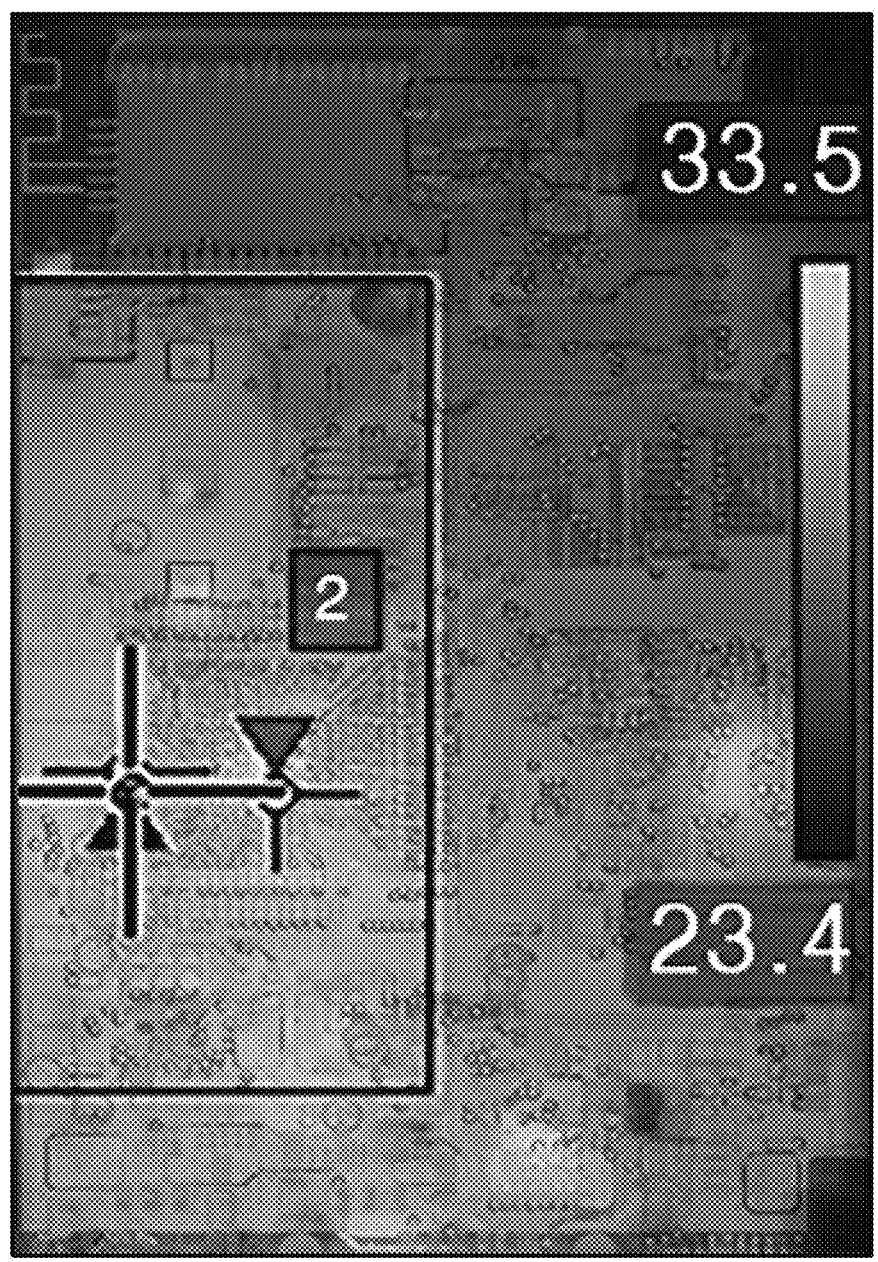
FIG. 2 is an example diagram illustrating an internal-temperature distribution pattern of a POC diagnostic device adaptable to environmental changes according to an embodiment of the present invention.
Figure 3:
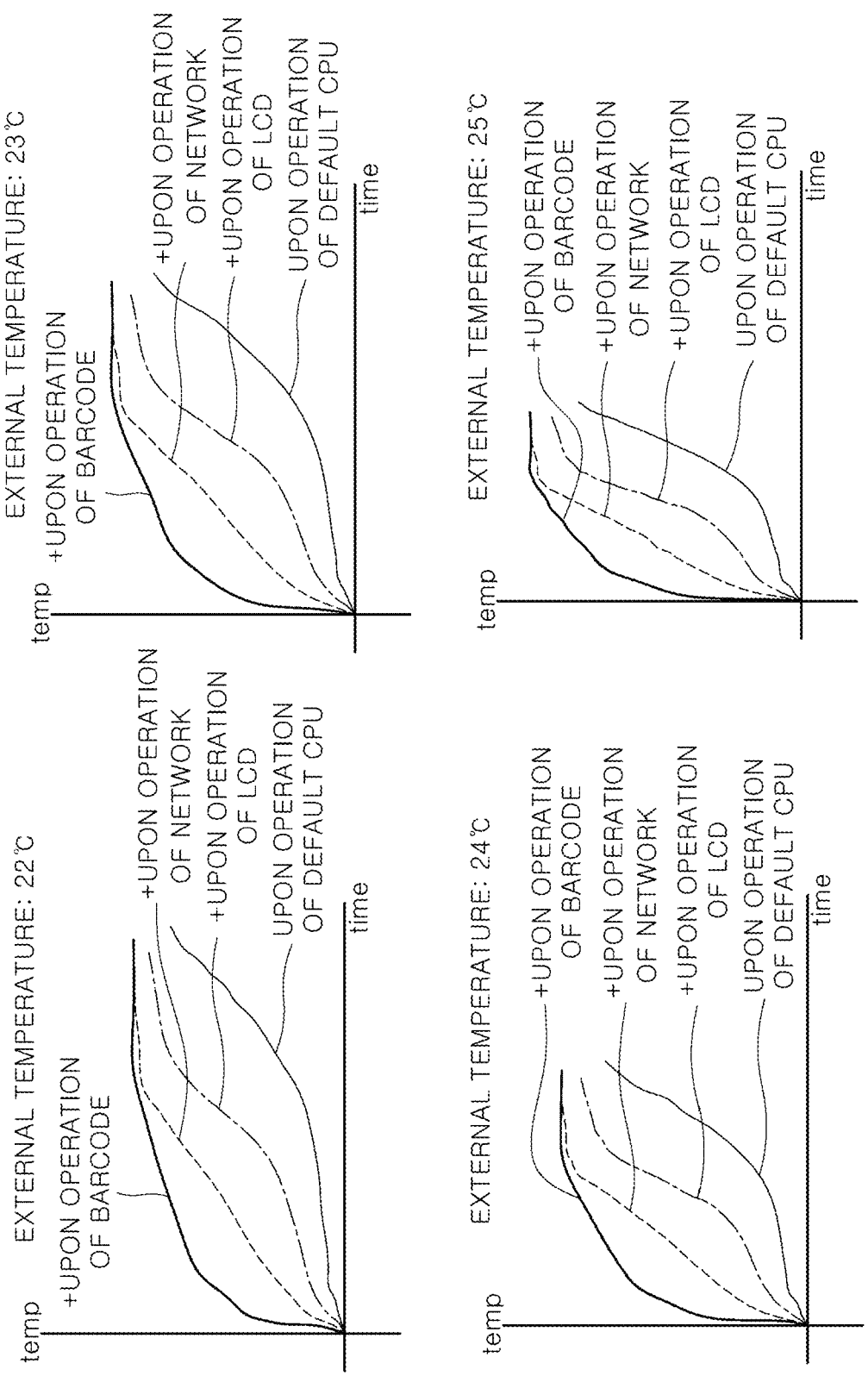
FIG. 3 is an example diagram illustrating a temperature pattern of a POC diagnostic device according to the activation of each module of a POC diagnostic device adaptable to environmental changes according to an embodiment of the present invention.

FIG. 1 is a block diagram showing a configuration of a POC diagnostic device adaptable to environmental changes according to an embodiment of the present invention, FIG. 2 is an example diagram illustrating an internal-temperature distribution pattern of the POC diagnostic device adaptable to environmental changes according to an embodiment of the present invention, and FIG. 3 is an example diagram illustrating a temperature pattern of a POC diagnostic device according to the activation of each module of the POC diagnostic device adaptable to environmental changes according to an embodiment of the present invention. The POC diagnostic device adaptable to environmental changes according to an embodiment of the present invention will be described with reference to FIGS. 1 to 3.

As shown in FIG. 1, the POC diagnostic device adaptable to environmental changes according to an embodiment of the present invention may include a control unit 100, a measurement unit 200, an information acquisition unit 300, and a plurality of modules 401, 402, and 403.

The measurement unit 200 may perform measurement for a POC diagnosis. For example, the measurement unit 200 may be configured to measure blood sugar (glucose) blood pressure, body temperature, oxygen saturation, an electrocardiogram, etc. of a person undergoing diagnostic examination (i.e., a patient). For example, the measurement unit 200 may be a blood sugar measurement unit (not shown) for measuring the blood sugar of a person undergoing diagnostic examination, and the blood sugar measurement unit may measure the blood sugar of a patient by analyzing a diagnostic strip inserted through a strip insertion unit (not shown). Such a method of measuring blood sugar is a well-known technique, and thus will not be described in detail.

Also, the measurement unit 200 may include a temperature adjustment unit (not show) capable of adjusting its own temperature. For example, the temperature adjustment unit may include a heater (e.g., a resistance-type heating element), and the control unit 100 may drive the heater to adjust the temperature of the measurement unit 200.

The information acquisition unit 300 may acquire environmental information of the POC diagnostic device. For example, the information acquisition unit 300 may include a location sensor such as a GPS receiver to acquire location information of the POC diagnostic device, may include an atmospheric pressure sensor to acquire atmospheric pressure in the vicinity of the POC diagnostic device, and may include a humidity sensor to acquire humidity information in the vicinity of the POC diagnostic device.

Also, the information acquisition unit 300 may include at least one temperature sensor, and the temperature sensor may be configured to detect temperatures at several internal points of or outside the POC diagnostic device. However, the external temperature measured by the temperature sensor is typically affected by the temperature of the POC diagnostic device itself. Thus, there may be a difference between the external temperature measured by the temperature sensor and a temperature in an atmosphere in which the POC diagnostic device is actually located or a temperature of a location where measurement takes place in the measurement unit 200.

In addition, the information acquisition unit 300 may include various sensors to acquire various kinds of environmental information of the POC diagnostic device.

The plurality of modules 401, 402, and 403 are modules for performing functions other than the measurement for the POC diagnosis and the acquisition of ambient environmental information and may be individually activated or deactivated.

Examples of the modules 401, 402, and 403 may include a display module for displaying information, a communication module for communicating with an external device, and a barcode module for recognizing a barcode. In addition, various other modules may be employed as the modules 401, 402, and 403.

The control unit 100 may predict the temperature of the measurement unit 200 on the basis of whether the plurality of modules 401, 402, and 403 are active or inactive and the environmental information (e.g., internal and external temperatures of the POC diagnostic device) acquired by means of the information acquisition unit 300.

The measurement unit 200 is exposed so that a strip or the like may be inserted thereinto. Thus, the temperature of the measurement unit 200 (i.e., the temperature at which a reaction for the measurement occurs) corresponds to the internal temperature or external temperature of the POC diagnostic device. Accordingly, the temperature of the measurement unit 200 appears to be a value close to the actual atmospheric temperature. However, the temperature of the measurement unit 200 does not correspond to the actual atmospheric temperature because of the influence of the temperature of the POC diagnostic device itself.

Also, the location of the temperature sensor of the information acquisition unit 300 that detects an external temperature of the POC diagnostic device cannot be exactly the same as the location of the measurement unit 200. Thus, an error may occur when it is assumed that the temperature acquired by the information acquisition unit 300 is the temperature of the measurement unit 200.

In this embodiment, the control unit 100 may predict the temperature of the measurement unit 200 on the basis of whether the plurality of modules 401, 402, and 403 are active or inactive and the internal and external temperatures of the POC diagnostic device.

In detail, as shown in FIG. 2, the internal temperature of the POC diagnostic device has a pattern in which values are different for each point. Accordingly, the difference between the temperature acquired by the information acquisition unit 300 and the temperature of the measurement unit 200 is determined depending on the location of the temperature sensor (for detecting an external temperature) and the location of the measurement unit 200 in the temperature distribution pattern of the POC diagnostic device.

Also, the temperature distribution pattern changes on the basis of whether the plurality of modules 401, 402, and 403 are active or inactive and a current internal temperature of the POC diagnostic device.

Accordingly, the control unit 100 may store information regarding the temperature distribution pattern depending on whether each module is active or for each internal temperature of the POC diagnostic device, and also may predict the current temperature of the measurement unit 200 on the basis of the information regarding the temperature distribution pattern, the internal and external temperatures of the POC diagnostic device acquired by the information acquisition unit 300, and whether each module is active.

Here, the information regarding the temperature distribution pattern may indicate information regarding a relationship between the temperature of the measurement unit 200 and the external temperature of the POC diagnostic device acquired by the information acquisition unit 300, and may be preset according to the specifications of the POC diagnostic device, the location of the temperature sensor, the location of the measurement unit 200, or the like and then stored in the control unit 100.

The control unit 100 may correct a measurement value of the measurement unit 200 on the basis of the predicted temperature of the measurement unit 200. For example, the control unit 100 may correct a blood sugar measurement value on the basis of the predicted temperature.

That is, as described above, the temperature of the measurement unit 200 (i.e., the temperature at the location where the reaction for the measurement occurs) is not easy to directly measure. Conventionally, a method of designing a complex sensor arrangement structure, a method of building the temperature sensor into a blood sugar strip, or the like was used. However, error is still present in such methods, and cost required for production or measurement rapidly increases when the complex structure is implemented or when the temperature sensor is built into the strip.

Unlike conventional methods, the control unit 100 predicts the temperature of the measurement unit 200 and corrects the measurement value for the POC diagnosis according to the present embodiment. Thus, it is possible to achieve an accurate POC diagnosis without needing to directly detect the temperature of the measurement unit 200.

The correction of the blood sugar measurement value on the basis of the temperature of the blood sugar measurement unit is widely used in the art, and thus a detailed description thereof will be omitted.

In addition, the control unit 100 may predict a future temperature change as well as the current temperature of the measurement unit 200.

That is, as can be seen from FIG. 3, a pattern of changes over time in the internal temperature of the POC diagnostic device may differ depending on the external temperature of the POC diagnostic device and whether each module is active. Accordingly, the control unit 100 may detect a change over time in the internal temperature of the POC diagnostic device and compare the change with predetermined patterns to predict a future change in the internal temperature of the POC diagnostic device.

A large change in external temperature may not occur on a timescale associated with a POC diagnosis (e.g., in units of minute). Accordingly, when it is assumed that there will be no change in the external temperature of the POC diagnostic device to be acquired by the information acquisition unit 300 at a future prediction time, the control unit 100 may predict a future temperature change of the measurement unit 200 through the above-described method of using a temperature distribution pattern.

The patterns of the temperature change of the POC diagnostic device according to whether the plurality of modules 401, 402, and 403 are each active or inactive and the external temperature of the POC diagnostic device may be prestored in the control unit 100, and the control unit 100 may be designed to predict a change in temperature up to a specific time.

The control unit 100 may control the POC diagnostic device on the basis of the predicted future temperature change of the measurement unit 200.

For example, when the temperature of the measurement unit 200 is predicted to rise above a first reference value within a first reference timeframe, the control unit 100 may deactivate at least one of the plurality of modules 401, 402, and 403.

That is, even when the control unit 100 predicts the temperature of the measurement unit 200 to compensate for a measurement value, there is a temperature range in which a more accurate measurement may be performed or a critical range in which a measurement may be performed.

Accordingly, when the temperature of the measurement unit 200 is predicted to rise, the control unit 100 may deactivate at least one of the plurality of modules 401, 402, and 403 to maintain the temperature of the measurement unit 200 at a specific level (e.g., less than 40° C.), thus enhancing accuracy of the measurement.

Also, when the deactivation is performed, the control unit 100 may select a module to be deactivated among the plurality of modules 401, 402, and 403 according to preset priorities, and the priorities may change depending on the detected internal temperature.

That is, it may be preset which module is preferentially deactivated according to the internal temperature of the POC diagnostic device, and the priorities may be designed in consideration of the importance of functions performed by the corresponding modules, an influence of the activation of the corresponding modules on the temperature change of the measurement unit 200, or the like.

Also, the control unit 100 may control the temperature adjustment unit of the measurement unit 200 on the basis of the predicted future temperature change of the measurement unit 200. For example, when the temperature of the measurement unit 200 is predicted to fall below a second reference value within a second reference timeframe, the control unit 100 may drive the heater of the temperature adjustment unit.

That is, when the temperature of the measurement unit 200 is predicted to fall, the control unit 100 may drive the heater to maintain the temperature of the measurement unit 200 at a specific level (e.g., greater than 20° C.), thus enhancing accuracy of the measurement.

Here, the first reference timeframe, the second reference timeframe, the first reference value, and the second reference value may be variously designed and preset according to the specifications of the POC diagnostic device. Preferably, the first reference value may be greater than the second reference value. Also, the first reference timeframe may be equal to the second reference timeframe.

Figure 4:
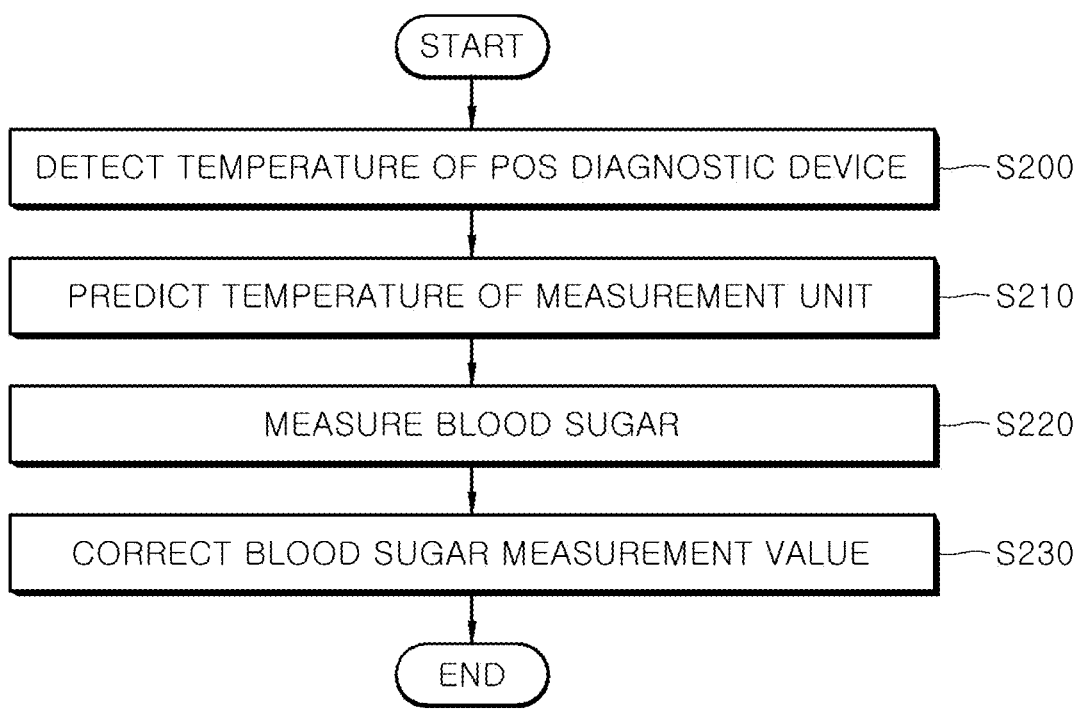
FIG. 4 is a flowchart illustrating a control method of a POC diagnostic device adaptable to environmental changes according to an embodiment of the present invention.

FIG. 4 is a flowchart illustrating a control method of the POC diagnostic device adaptable to environmental changes according to an embodiment of the present invention. The control method of the POC diagnostic device adaptable to environmental changes according to an embodiment of the present invention will be described below with reference to FIG. 4.

As shown in FIG. 4, first, a control unit 100 detects a temperature of the POC diagnostic device (S200). For example, the control unit 100 may detect internal and external temperatures of the POC diagnostic device. When temperatures are detected at many points by means of many temperature sensors, it is possible to enhance accuracy of the prediction of the temperature of measurement unit 200.

Subsequently, the control unit 100 predicts a temperature of a measurement unit 200 on the basis of the temperature detected in operation S200 (S210). In this case, the control unit 100 may predict the temperature of the measurement unit 200 on the basis of the temperature detected in operation S200 and whether a plurality of modules 401, 402, and 403 are each active or inactive.

After operation S210, the control unit 100 measures blood sugar by means of the measurement unit 200 (S220). That is, the control unit 100 may measure blood sugar of a person undergoing diagnostic examination by means of a blood sugar measurement unit included in the measurement unit 200.

The temperature prediction for and the blood sugar measurement of the measurement unit 200 are not limited to the above-described sequence of the present invention, and thus operation S200 may be performed before or at the same time as operation S210.

Subsequently, the control unit 100 corrects a measurement value measured in operation S220 on the basis of the temperature of the measurement unit 200 predicted in operation S210 (S230). That is, the control unit 100 may correct the measurement value on the basis of the temperature of the measurement unit 200, thereby enabling a blood sugar measurement value to be accurately acquired and thus enhancing the accuracy of diabetes diagnosis of the POC diagnostic device.

Figure 5:
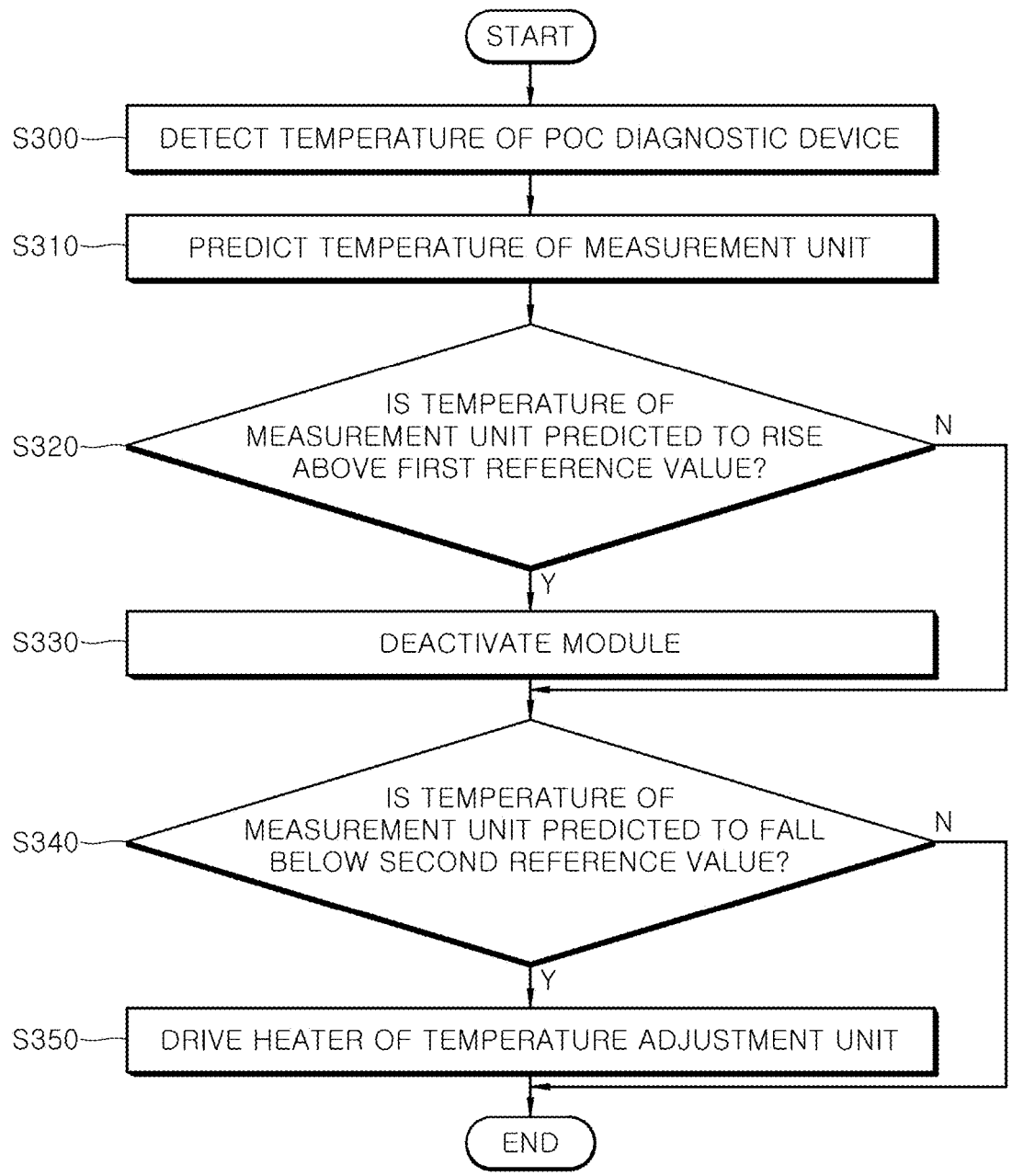
FIG. 5 is a flowchart illustrating a control method of a POC diagnostic device adaptable to environmental changes according to another embodiment of the present invention.

FIG. 5 is a flowchart illustrating a control method of the POC diagnostic device adaptable to an environmental change according to another embodiment of the present invention. The control method of the POC diagnostic device adaptable to an environmental change according to another embodiment of the present invention will be described below with reference to FIG. 5.

As shown in FIG. 5, first, a control unit 100 detects a temperature of the POC diagnostic device (S300) and predicts a temperature of a measurement unit 200 on the basis of the detected temperature (S310). In this case, the control unit 100 may predict the temperature of the measurement unit 200 on the basis of the temperature detected in operation S300 and whether a plurality of modules 401, 402, and 403 are each active or inactive. The control unit 100 may even predict a future temperature change as well as a current temperature of the measurement unit 200 by utilizing a change over time in an internal temperature of the POC diagnostic device Subsequently, when the temperature of the measurement unit 200 is predicted to rise above a first reference value within a specific timeframe (S320), the control unit 100 may deactivate at least one of the plurality of modules 401, 402, and 403 (S330).

Accordingly, when the temperature of the measurement unit 200 is predicted to rise, the control unit 100 may deactivate at least one of the plurality of modules 401, 402, and 403 to maintain the temperature of the measurement unit 200 at a specific level (e.g., less than 40° C.), thus enhancing accuracy of the measurement.

In this case, the control unit 100 checks whether there are deactivatable modules, and deactivates at least one of the modules according to preset priorities when the modules are deactivatable. For example, when all of the plurality of modules 401, 402, and 403 are inactive, there is no deactivatable module.

Also, when the temperature of the measurement unit 200 is predicted to fall below a second reference value within a specific timeframe (S340), the control unit 100 may drive a heater of a temperature adjustment unit included in the measurement unit 200 (S350).

That is, when the temperature of the measurement unit 200 is predicted to fall, the control unit 100 may drive the heater to maintain the temperature of the measurement unit 200 at a specific level (e.g., greater than 20° C.), thus enhancing accuracy of the measurement.

With the POC diagnostic device adaptable to environmental changes and the control method thereof according to embodiments of the present invention, as described above, it is possible to enhance the accuracy of a POC diagnosis by predicting a temperature of a measurement unit configured to perform the POC diagnosis to correct a measurement value or maintain the temperature of the measurement unit.

With the POC diagnostic device adaptable to environmental changes and the control method thereof according to embodiments of the present invention, it is possible to enhance the accuracy of a POC diagnosis by predicting a temperature of a measurement unit configured to perform the POC diagnosis to correct a measurement value.

While the present invention has been described with reference to embodiments shown in the accompanying drawings, it should be understood by those skilled in the art that the embodiments are merely illustrative of the invention and that various modifications and equivalents may be made without departing from the spirit and scope of the invention. Accordingly, the technical scope of the present invention should be determined only by the appended claims.

What is claimed is:

1. A point-of-care (POC) diagnostic device adaptable to environmental changes, the POC diagnostic device comprising:
    a measurement unit configured to perform a POC diagnosis;
    temperature sensors configured to detect internal and external temperatures of the POC diagnostic device, respectively;
    a plurality of modules capable of being individually activated or deactivated; and
    a control unit configured to predict a present temperature and a future temperature change of the measurement unit and correct a measurement value of the measurement unit or control the POC diagnostic device on the basis of the predicted temperature of the measurement unit,
    wherein the control unit predicts the present temperature of the measurement unit on the basis of whether the plurality of modules are each activated or deactivated, detection values of the temperature sensors, and temperature distribution patterns,
    wherein the control unit predicts a future internal temperature change of the POC diagnostic device on the basis of patterns of the temperature change of the POC diagnostic device, and predicts the future temperature change of the measurement unit on the basis of the future internal temperature change of the POC diagnostic device and an assumption that there will be no change in the external temperature of the POC diagnostic device,
    wherein the temperature distribution patterns are stored in the control unit for each internal temperature of the POC diagnostic device depending on whether the plurality of modules are each activated or deactivated, and indicate a relationship between a temperature of the measurement unit and an external temperature of the POC diagnostic device, and
    wherein patterns of the temperature change of the POC diagnostic device are stored in the control unit for each external temperature of the POC diagnostic device depending on whether the plurality of modules are each activated or deactivated, and indicate a relationship between an internal temperature and an external temperature of the POC diagnostic device.

2. The POC diagnostic device of claim 1, wherein the control unit controls the activation or deactivation of the plurality of modules on the basis of the predicted temperature of the measurement unit.

3. The POC diagnostic device of claim 2, wherein the control unit deactivates at least one of the plurality of modules when the temperature of the measurement unit is predicted to rise above a first reference value within a first reference timeframe.

4. The POC diagnostic device of claim 3, wherein the control unit determines modules to be deactivated according to preset priorities.

5. The POC diagnostic device of claim 1, wherein the measurement unit comprises a temperature adjustment unit configured to adjust the temperature of the measurement unit, and the control unit controls the temperature adjustment unit on the basis of the predicted temperature of the measurement unit.

6. The POC diagnostic device of claim 5, wherein:
    the temperature adjustment unit comprises a heater; and
    the control unit drives the heater when the temperature of the measurement unit is predicted to fall below a second reference value within a second reference timeframe.

7. The POC diagnostic device of claim 1, wherein the POC diagnostic device further comprises a location sensor configured to acquire location information of the POC diagnostic device, an atmospheric pressure sensor configured to acquire atmospheric pressure information, and a humidity sensor configured to acquire humidity information.

8. The POC diagnostic device of claim 1, wherein the plurality of modules includes a display module configured to display information, a communication module configured to communicate with an external device, and a barcode module configured to recognize a barcode.

9. The POC diagnostic device of claim 1, wherein the measurement unit comprises a blood sugar measurement unit configured to measure blood sugar of a person undergoing diagnostic examination.

10. A control method of a point-of-care (POC) diagnostic device adaptable to environmental changes, the control method comprising:
    acquiring internal and external temperatures of the POC diagnostic device utilizing temperature sensors;
    predicting a present temperature and a future temperature change of a measurement unit configured to perform a POC diagnosis utilizing a control unit;
    controlling the POC diagnostic device utilizing the control unit when the temperature of the measurement unit is predicted to rise above a first reference value within a first reference timeframe or to fall below a second reference value within a second reference timeframe;
    performing a measurement for the POC diagnosis utilizing the measurement unit; and
    correcting a measurement value obtained by the measurement unit on the basis of the predicted temperature of the measurement unit utilizing the control unit,
    wherein the POC diagnostic device comprises a plurality of modules capable of being individually activated or deactivated,
    wherein the predicting step comprises: predicting the present temperature of the measurement unit on the basis of whether the plurality of modules are each activated or deactivated, detection values of the temperature sensors, and temperature distribution patterns, predicting a future internal temperature change of the POC diagnostic device on the basis of patterns of the temperature change of the POC diagnostic device, and predicting the future temperature change of the measurement unit on the basis of the future internal temperature change of the POC diagnostic device and an assumption that there will be no change in the external temperature of the POC diagnostic device, wherein the temperature distribution patterns are stored in the control unit for each internal temperature of the POC diagnostic device depending on whether the plurality of modules are each activated or deactivated, and indicate a relationship between a temperature of the measurement unit and an external temperature of the POC diagnostic device, and wherein patterns of the temperature change of the POC diagnostic device are stored in the control unit for each external temperature of the POC diagnostic device depending on whether the plurality of modules are each activated or deactivated, and indicate a relationship between an internal temperature and an external temperature of the POC diagnostic device.

11. The control method of claim 10, wherein:
the controlling of the POC diagnostic device comprises deactivating at least one of the plurality of modules when the temperature of the measurement unit is predicted to rise above the first reference value within the first reference timeframe.

12. The control method of claim 11, wherein the deactivation of at least one of the plurality of modules comprises:
checking whether there are deactivatable modules; and
deactivating at least one of the modules according to preset priorities when the modules are deactivatable.

13. The control method of claim 10, wherein:
the measurement unit comprises a heater; and
the controlling of the POC diagnostic device comprises driving the heater when the temperature of the measurement unit is predicted to fall below the second reference value within the second reference timeframe.

14. The control method of claim 10, wherein the performing of a measurement for the POC diagnosis utilizing the measurement unit comprises measuring the blood sugar of a person undergoing diagnostic examination.

* * * * *